(12) United States Patent
Mikami

(10) Patent No.: US 10,770,811 B2
(45) Date of Patent: Sep. 8, 2020

(54) CABLE STRUCTURE, MOUNT MODULE, AND ENDOSCOPE

(71) Applicant: OLYMPUS CORPORATION, Tokyo (JP)

(72) Inventor: Masato Mikami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/438,650

(22) Filed: Jun. 12, 2019

(65) Prior Publication Data

US 2019/0296537 A1 Sep. 26, 2019

Related U.S. Application Data

(63) Continuation of application No. PCT/JP2016/088548, filed on Dec. 22, 2016.

(51) Int. Cl.
*H01R 12/53* (2011.01)
*A61B 1/00* (2006.01)
(Continued)

(52) U.S. Cl.
CPC .......... *H01R 12/53* (2013.01); *A61B 1/00114* (2013.01); *A61B 1/00124* (2013.01); *A61B 1/04* (2013.01); *H01R 4/027* (2013.01); *H01R 9/2416* (2013.01); *H01R 9/2475* (2013.01); *H01R 43/28* (2013.01); *H02G 15/02* (2013.01); *H02G 15/025* (2013.01); *H02G 15/06* (2013.01); *H04N 5/2251* (2013.01); *H04N 2005/2255* (2013.01)

(58) Field of Classification Search
CPC ..................................................... H01R 12/53
See application file for complete search history.

(56) References Cited

U.S. PATENT DOCUMENTS 5,415,567 A 5/1995 Fusselman et al.
6,652,325 B2 * 11/2003 Tharp ................ H01R 12/721
439/457
(Continued)

FOREIGN PATENT DOCUMENTS

JP 48-1779 A 1/1973
JP 8-509837 A 10/1996
(Continued)

OTHER PUBLICATIONS

International Search Report dated Feb. 28, 2017 received in PCT/JP2016/088548.

*Primary Examiner* — James Harvey
(74) *Attorney, Agent, or Firm* — Scully, Scott, Murphy & Presser, P.C.

(57) ABSTRACT

A cable structure includes: a plurality of cables each including a conductor part and an electrically-insulative covering part, each conductor part being exposed in a part where the covering part at one end thereof is removed; and a cable fixing part formed by resin molding and configured to hold the plurality of cables while the ends of the plurality of cables exposing the conductor parts are aligned, wherein the cable fixing part includes a bottom face opening formed on a bottom face side facing a member to which the cables are connected and a top face opening formed on a top face side opposing the bottom face, the bottom face side and the top face side exposing the conductor parts.

14 Claims, 11 Drawing Sheets

(51) Int. Cl.
*H01R 4/02* (2006.01)
*H01R 43/28* (2006.01)
*H02G 15/02* (2006.01)
*H02G 15/06* (2006.01)
*H04N 5/225* (2006.01)
*A61B 1/04* (2006.01)
*H01R 9/24* (2006.01)

(56) References Cited

U.S. PATENT DOCUMENTS

| | | | | |
|---|---|---|---|---|
| 7,270,571 | B1* | 9/2007 | Huang | H01R 4/023 |
| | | | | 439/607.45 |
| 7,357,664 | B2* | 4/2008 | Hsu | H01R 43/0221 |
| | | | | 439/499 |
| 7,549,895 | B2* | 6/2009 | Kondo | H01R 4/027 |
| | | | | 439/579 |
| 8,100,729 | B2* | 1/2012 | Chen | H01R 9/03 |
| | | | | 439/719 |
| 2006/0234556 | A1* | 10/2006 | Wu | H01R 12/721 |
| | | | | 439/607.05 |
| 2010/0087087 | A1* | 4/2010 | Yeh | H01R 12/592 |
| | | | | 439/493 |
| 2011/0042140 | A1 | 2/2011 | Nakamura et al. | |
| 2013/0244453 | A1* | 9/2013 | Sakamoto | H01R 12/712 |
| | | | | 439/55 |
| 2016/0005513 | A1* | 1/2016 | Sekido | H01B 7/0216 |
| | | | | 174/74 R |
| 2018/0115093 | A1* | 4/2018 | Gross | H01R 12/53 |
| 2019/0296537 | A1* | 9/2019 | Mikami | H01R 43/28 |
| 2019/0393656 | A1* | 12/2019 | Wu | H05K 1/00 |

FOREIGN PATENT DOCUMENTS

| | | |
|---|---|---|
| JP | 11-031560 A | 2/1999 |
| JP | 11-329098 A | 11/1999 |
| JP | 2011-045173 A | 3/2011 |
| JP | 5583372 B2 | 9/2014 |
| WO | 94/26004 A1 | 11/1994 |
| WO | 2009/139041 A1 | 11/2009 |

* cited by examiner

US 10,770,811 B2

CABLE STRUCTURE, MOUNT MODULE, AND ENDOSCOPE

CROSS-REFERENCE TO RELATED APPLICATION

This application is a continuation of PCT International Application No. PCT/JP2016/088548 filed on Dec. 22, 2016, which designates the United States, incorporated herein by reference.

BACKGROUND

The present disclosure relates to a cable structure, a mount module, and an endoscope.

In the related art, endoscopes that are inserted into a subject and observe an observed region and the like are known and are widely used in the medical field and the like. In such an endoscope, a cable assembly putting together a plurality of cables is used and is connected to a circuit board while an outside cover thereof is removed. As for a distal end part of endoscopes, there is a demand for keeping the diameter and the length small, in consideration of easiness to introduce an endoscope into a patient.

For the purpose of miniaturizing the distal end part of an endoscope, a technique has been disclosed by which, for example, distal end parts of a plurality of coaxial cables are fixed by using a cable fixing member, while a step part such as an opening part or the like that exposes core wires and shield wires are provided on such a face of the cable fixing member that opposes a connection surface of the circuit board, so as to collectively connect the plurality of coaxial cables by fitting the step part into an electrode part (see Japanese Patent No. 5,583,372, for example).

SUMMARY

There is a need for a cable structure, a mount module, and an endoscope that make it possible to connect a plurality of cables to a circuit board in an easy and quick manner, while enabling miniaturization.

A cable structure according to some embodiments of the present disclosure includes: a plurality of cables each including a conductor part and an electrically-insulative covering part, each conductor part being exposed in a part where the covering part at one end thereof is removed; and a cable fixing part formed by resin molding and configured to hold the plurality of cables while the ends of the plurality of cables exposing the conductor parts are aligned, wherein the cable fixing part includes a bottom face opening formed on a bottom face side facing a member to which the cables are connected and a top face opening formed on a top face side opposing the bottom face, the bottom face side and the top face side exposing the conductor parts.

The above and other features, advantages and technical and industrial significance of this disclosure will be better understood by reading the following detailed description of exemplary embodiments of the disclosure, when considered in connection with the accompanying drawings.

DETAILED DESCRIPTION

Figure 1:
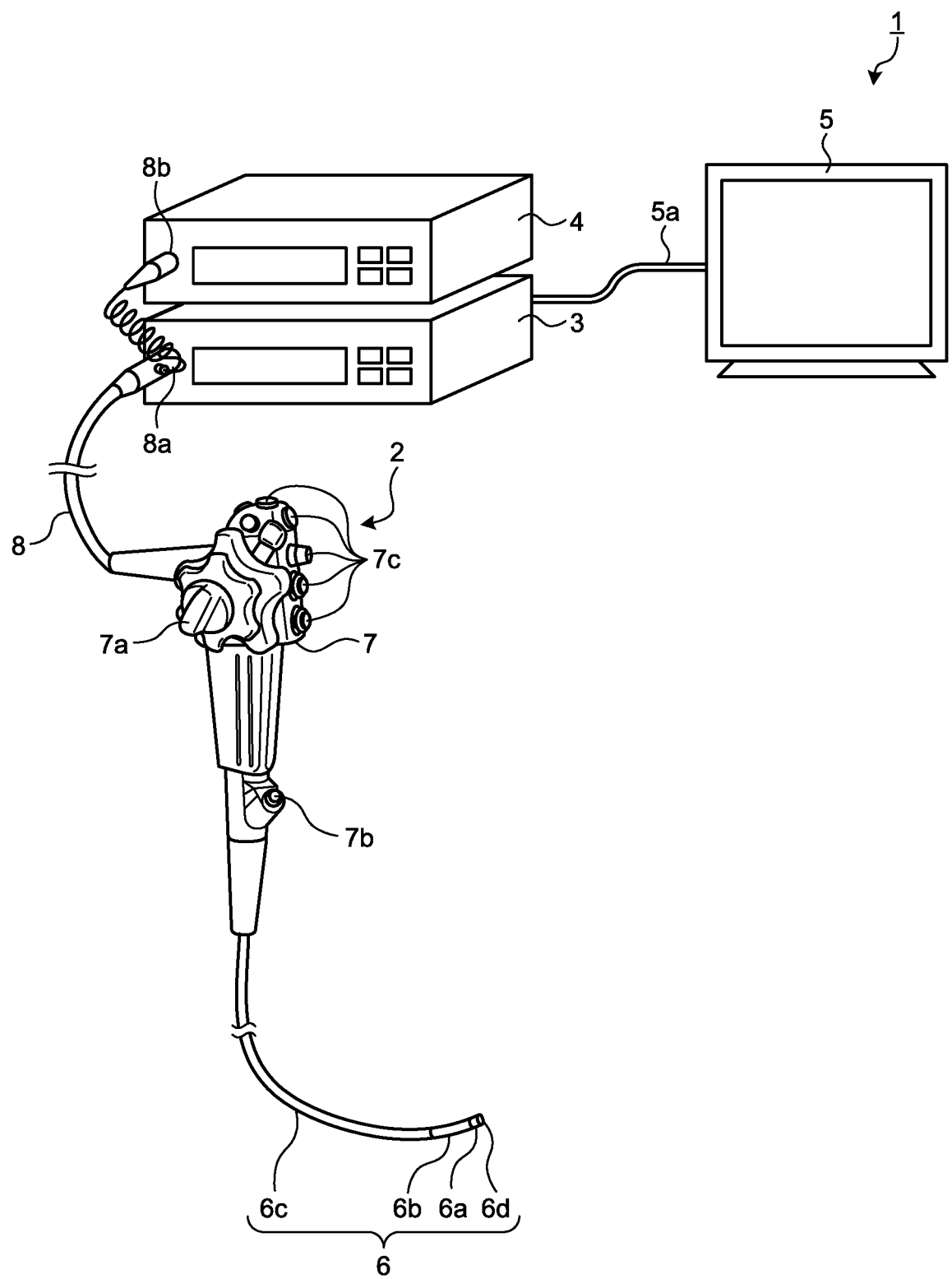
FIG. 1 is a drawing schematically illustrating an overall configuration of an endoscope system according to a first embodiment.

In the explanation below, an endoscope system including an imaging device having a cable structure will be explained, as embodiments for carrying out the present disclosure (hereinafter, "the embodiments"). Further, the present disclosure is not limited to the embodiments. In the drawings, mutually the same parts are referred to by using the same reference characters. Further, it should be noted that the drawings are schematic, and the relationship between the thickness and the width of each member, the scales of the members, and the like may be different in reality. Also, among the drawings, the dimensions and the scales may partially be different from one another.

FIG. 1 is a drawing schematically illustrating an overall configuration of an endoscope system 1 according to a first embodiment. As illustrated in FIG. 1, the endoscope system 1 according to the first embodiment includes: an endoscope 2 that is introduced into a subject, images the inside of the body of the subject, and generates an image signal of the inside of the subject; an information processing device 3 (an external processor) that performs a predetermined image processing process on the image signal captured by the endoscope 2 and also controls functional units of the endoscope system 1; a light source device 4 that generates illumination light of the endoscope 2; and a display device 5 that displays, as an image, the image signal resulting from the image processing process performed by the information processing device 3.

The endoscope 2 includes: an insertion part 6 to be inserted into the subject; an operation part 7 that is positioned on the side of a proximal end part of the insertion part 6 and is held by a practitioner; and a universal cord 8 that is flexible and extends from and retracts into the operation part 7.

The insertion part 6 is realized by using an illumination fiber (a light guide cable), an electric cable, and an optical fiber, or the like. The insertion part 6 includes: a distal end part 6a having an imaging unit (explained) built therein; a bending part 6b structured by using a plurality of bend pieces so as to be bendable; and a flexible tube part 6c that is flexible and is provided on the side of the proximal end part of the bending part 6b. Provided in the distal end part 6a are an illumination part that illuminates the inside of the subject via an illumination lens; an observation part that images the inside of the subject; an opening part that allows communication through a treatment tool channel, and an air-supply/fluid-supply nozzle (not illustrated).

The operation part 7 includes: a bending knob 7a that bends the bending part 6b in up-and-down directions and left-and-right directions; a treatment tool insertion part 7b through which a treatment tool such as surgical forceps, a laser scalpel, or the like is inserted into a body cavity of the subject; and a plurality of switch parts 7c used for operating peripheral devices such as the information processing device 3, the light source device 4, an air supply device, a fluid supply device, a gas supply device, and the like. The treatment tool inserted through the treatment tool insertion part 7b is routed through the treatment tool channel provided on the inside and is exposed to the outside through an opening part 6d provided at the distal end of the insertion part 6.

The universal cord 8 is structured by using an illumination fiber, a cable, and the like. The universal cord 8 is branched at the proximal end thereof, so that one of the branched end parts serves as a connector 8a, whereas the other end part serves as a connector 8b. The connector 8a can detachably be attached to a connector of the information processing device 3. The connector 8b can detachably be attached to the light source device 4. The universal cord 8 propagates the illumination light emitted from the light source device 4 to the distal end part 6a via the connector 8b and the illumination fiber. Further, the universal cord 8 transfers the image signal captured by the imaging device (explained later) to the information processing device 3 via the cable and the connector 8a.

The information processing device 3 performs the predetermined image processing process on the image signal output from the connector 8a and controls the entirety of the endoscope system 1.

The light source device 4 is structured by using a light source that emits light, a condenser lens, or the like. Under the control of the information processing device 3, the light source device 4 emits the light from the light source and supplies the light as the illumination light for the inside of the subject serving as an imaged object, to the endoscope 2 connected via the connector 8b and the illumination fiber of the universal cord 8.

The display device 5 is structured by using a display monitor employing liquid crystals, organic electroluminescence (EL), or the like. Via a picture cable 5a, the display device 5 displays various types of information including the image on which the predetermined image processing process has been performed by the information processing device 3. As a result, the practitioner is able to observe a desired position inside the subject and to assess properties thereof, by operating the endoscope 2 while viewing the image (an in-vivo image) displayed by the display device 5.

Figure 2:
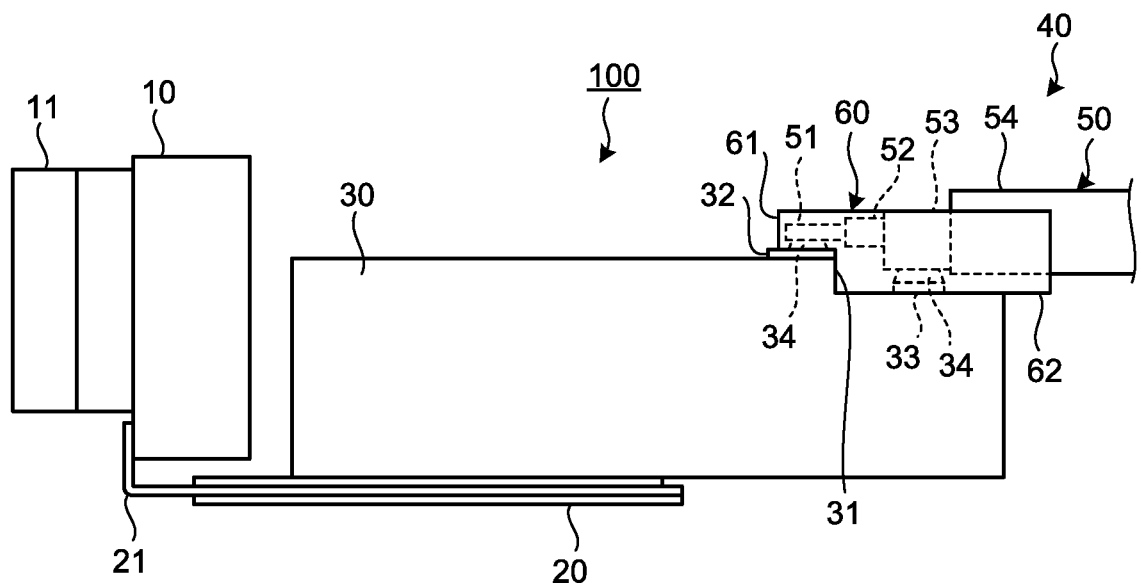
FIG. 2 is a side view of an imaging device used in the endoscope illustrated in FIG. 1.
Figure 3:
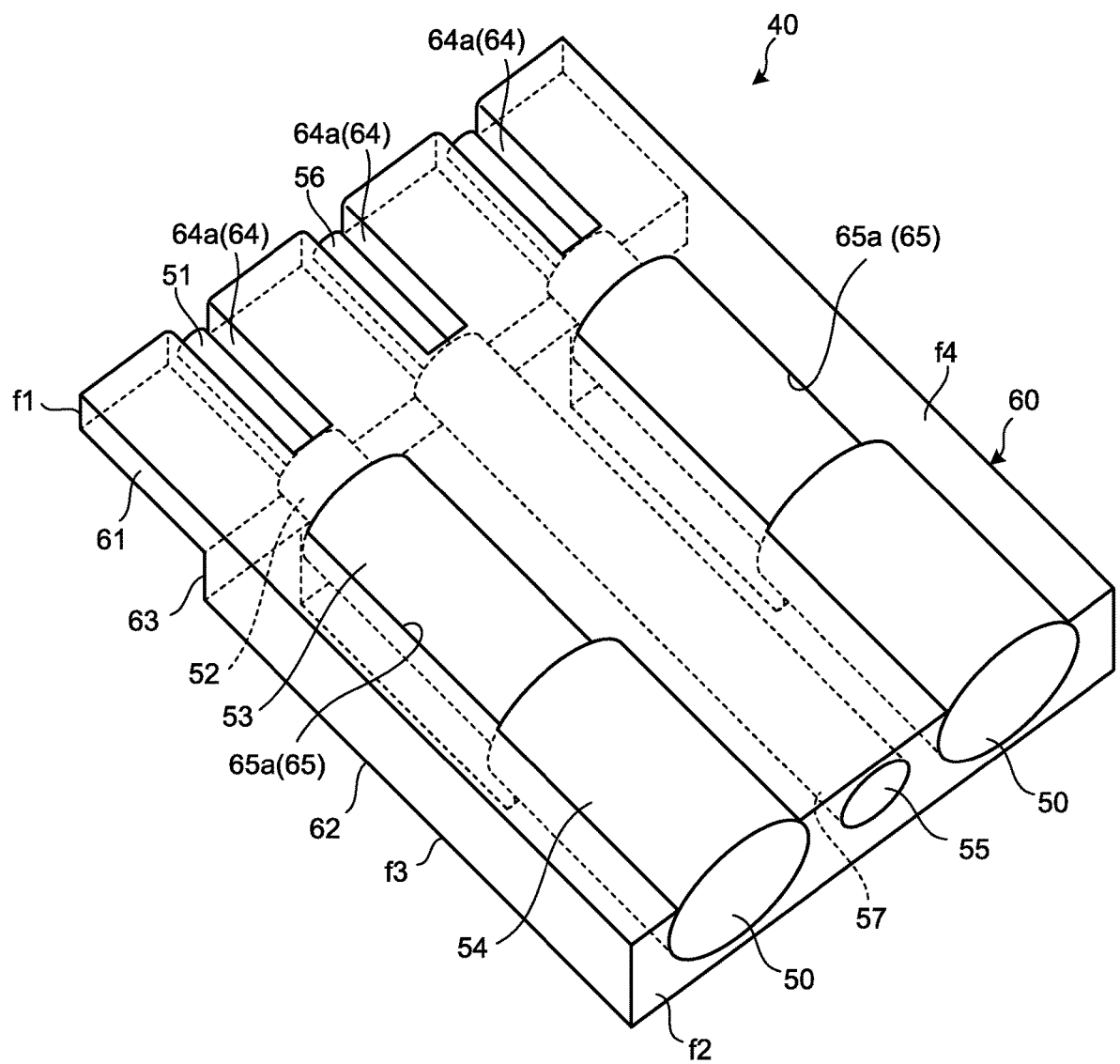
FIG. 3 is a perspective view of a cable structure used in the endoscope illustrated in FIG. 1.
Figure 4:
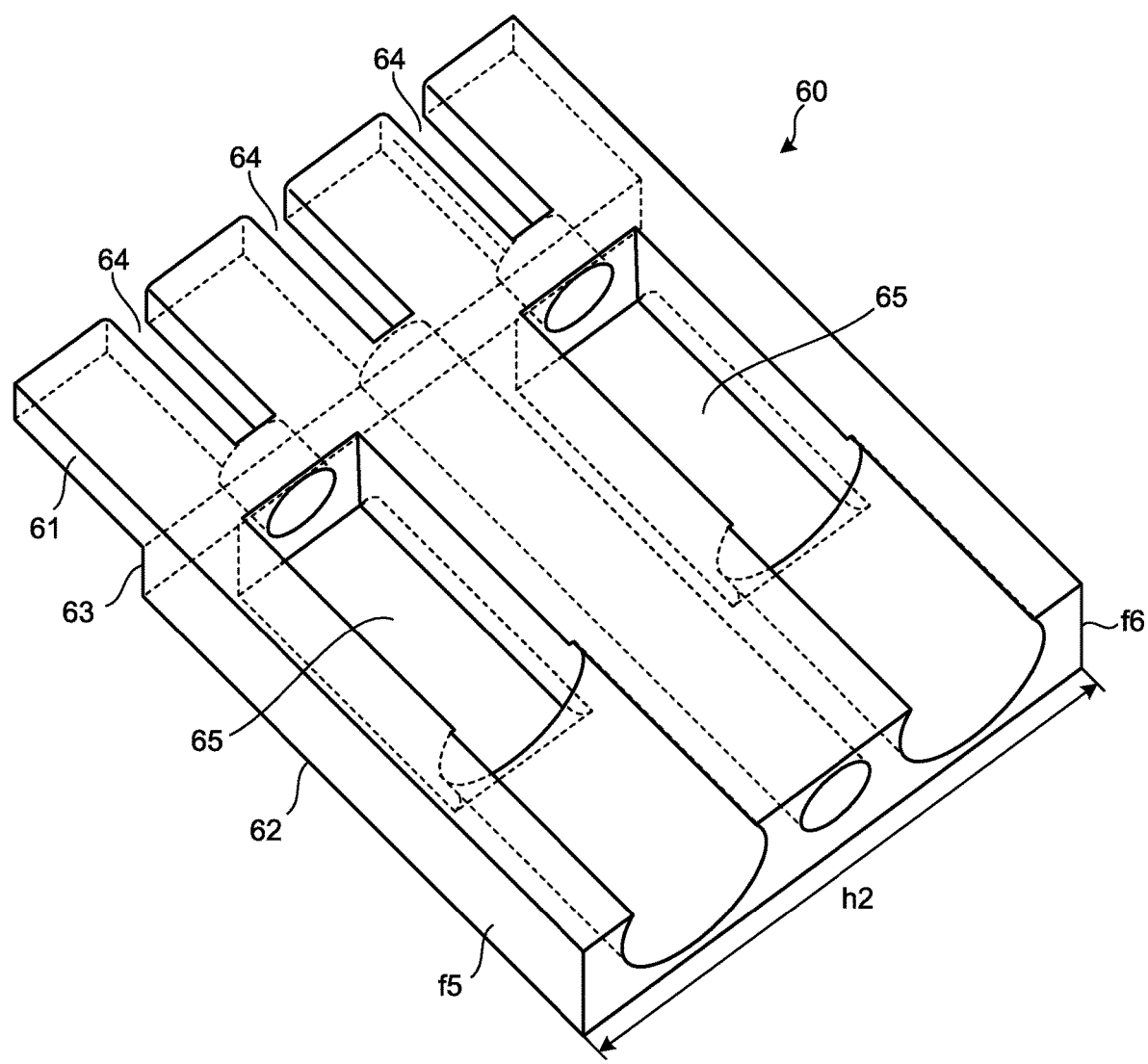
FIG. 4 is a perspective view of only the cable fixing part illustrated in FIG. 3.
Figure 5:
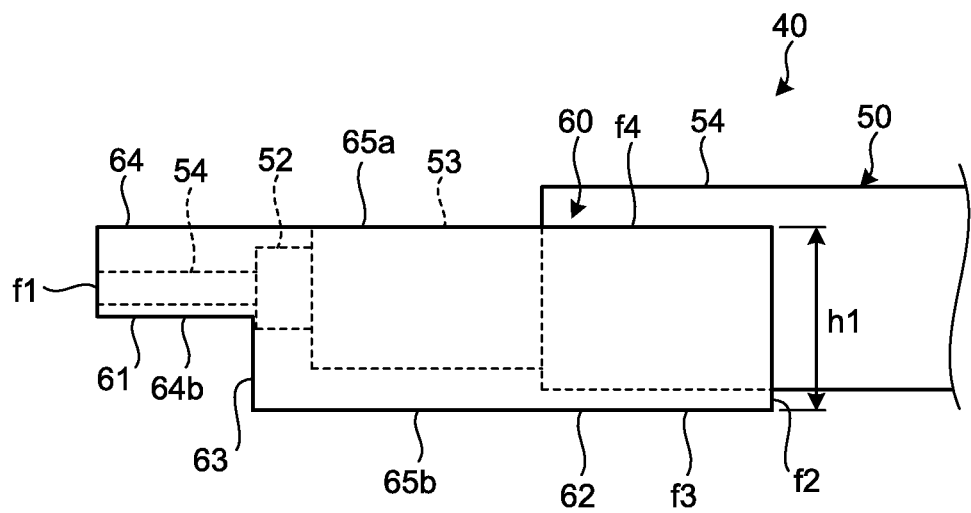
FIG. 5 is a side view of the cable structure illustrated in FIG. 3.
Figure 6:
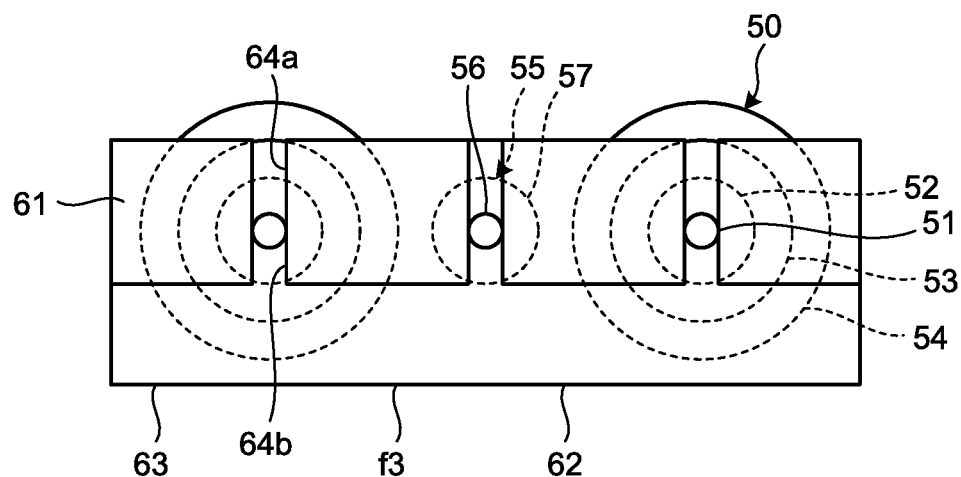
FIG. 6 is a front view of the cable structure illustrated in FIG. 3.
Figure 7:
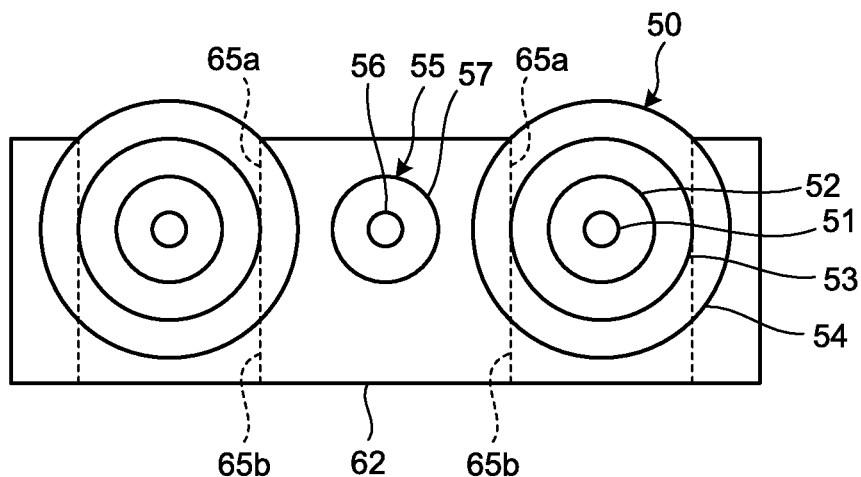
FIG. 7 is a rear view of the cable structure illustrated in FIG. 3.

Next, a configuration of the imaging device will be explained in detail. FIG. 2 is a side view of an imaging device 100 used in the endoscope 2 illustrated in FIG. 1. FIG. 3 is a perspective view of a cable structure 40 used in the endoscope 2. FIG. 4 is a perspective view of only a cable fixing part 60 illustrated in FIG. 3. FIG. 5 is a side view of the cable structure 40. FIG. 6 is a front view of the cable structure 40 (from a front side f1). FIG. 7 is a rear view of the cable structure 40 (from a rear side f2; a simple cable 55 and coaxial cables 50 are shown in cross-sections thereof).

The imaging device 100 includes an imaging element 10, a first circuit board 20, a second circuit board 30, and the cable structure 40.

The imaging element 10 has a sheet of cover glass 11 pasted thereon to protect a light receiving part. The first circuit board 20 is a flexible printed circuit board (hereinafter, "FPC board"). The first circuit board 20 is arranged so as to extend from the imaging element 10 along an optical axis direction, while an inner lead 21 is connected to an electrode pad (not illustrated) of the imaging element 10.

The second circuit board 30 is a laminated circuit board and has mounted thereon or built therein electronic component parts (not illustrated) structuring a driving circuit of the imaging element 10. The second circuit board 30 also has formed therein one or more vias (not illustrated) that realize electrical conduction between a plurality of conductive layers. Formed at the proximal end of the second circuit board 30 are: a core wire connection electrode 32 to which core wires 56 and 51 of the simple cable 55 and the coaxial cables 50 are to be connected; and a shield wire connection electrode 33 to which shield wires 53 of the coaxial cables 50 are to be connected. Further, formed between the core wire connection electrode 32 and the shield wire connection electrode 33 of the second circuit board 30 is a board step part 31 arranged in a direction orthogonal to the optical axis direction.

The cable structure 40 includes: the one simple cable 55, the two coaxial cables 50, and a cable fixing part 60 that holds the simple cable 55 and the coaxial cables 50 in an aligned state.

As for the simple cable 55, the core wire 56 serving as a conductor part is covered by an electrically-insulative (hereinafter, "insulative") outer covering 57, while the outer covering 57 at one end is removed so as to expose the core wire 56.

Each of the coaxial cables 50 includes the core wire 51 serving as a conductor part, an inner insulative member 52 covering the core wire 51, the shield wire 53 serving as a conductor part and being formed around the inner insulative member 52, and an outer insulative member 54 covering the shield wire 53. At one end of each of the coaxial cables 50, certain sections are removed so as to expose the core wire 51, the inner insulative member 52, and the shield wire 53.

The cable fixing part 60 is configured by using resin that is shaped by pouring melted resin into a molding frame while the simple cable 55 and the coaxial cables 50 are fixed to the inside of the molding frame by using a jig or the like. The cable fixing part 60 includes: a first fixing part 61 that fixes the core wire 56 of the simple cable 55 and the core wires 51 of the coaxial cables 50; and a second fixing part 62 that fixes the outer covering 57 positioned on the proximal end side relative to the exposed core wire 56 of the simple cable 55, as well as the inner insulative members 52, the shield wires 53, and the outer insulative members 54 of the coaxial cables 50.

The first fixing part 61 has first openings 64 formed therein. From the inside of the first openings 64, the core wire 56 of the simple cable 55 and the core wires 51 of the coaxial cables 50 are exposed. The core wires 56 and 51 are exposed from a top face f4 side (first top face openings 64a) and from a bottom face f3 side (first bottom face openings 64b) of the first openings 64. The core wire 56 of the simple cable 55 and the core wires 51 of the coaxial cables 50 are, as illustrated in FIG. 6, arranged so as to be positioned at an equal distance from the bottom face f3 side of the first fixing part 61. Arranging the core wires 56 and 51 to be positioned at the equal distance from the bottom face f3 side of the first fixing part 61 makes the connecting work easy when establishing a connection to the core wire connection electrode 32 of the second circuit board 30.

The second fixing part 62 has second openings 65 formed therein. From the inside of the second openings 65, the shield wires 53 of the coaxial cables 50 are exposed. The shield wires 53 are exposed from the top face f4 side (second top face openings 65a) and from the bottom face f3 side (second bottom face openings 65b) of the second openings 65.

A step part 63 is formed on the bottom face f3 side of the cable fixing part 60, between the first fixing part 61 and the second fixing part 62.

Figure 8:
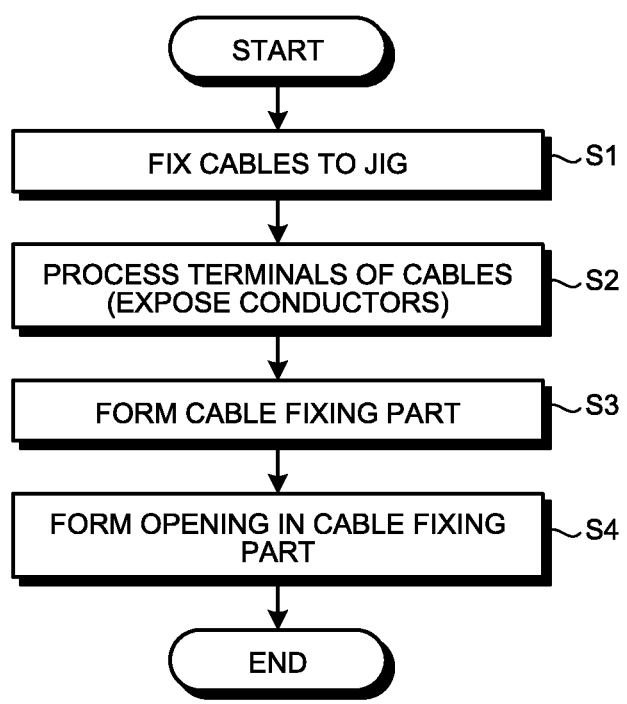
FIG. 8 is a flowchart for explaining a manufacturing method of the cable structure according to the first embodiment.

Next, a method of manufacturing the cable structure 40 will be explained with reference to drawings. FIG. 8 is a flowchart for explaining the method of manufacturing the cable structure according to the first embodiment.

First, the simple cable 55 and the coaxial cables 50 are fixed to a jig tool (step S1). After the cables are fixed, a terminal processing process (a conductor exposing process) is performed by removing the outer covering 57 of the simple cable 55 so as to expose the core wire 56, and also, removing the inner insulative members 52, the shield wires 53, and the outer insulative members 54 so as to expose the core wires 51, the inner insulative members 52, and the shield wires 53 of the coaxial cables 50 from the end parts (step S2). By performing the cable terminal processing process while the cables are fixed by the jig tool, it is possible to easily adjust the lengths of the exposed parts.

The cable fixing part 60 is formed by arranging the simple cable 55 and the coaxial cables 50 that are in the fixed state to be positioned on the inside of the molding frame, filling the molding frame with melted resin supplied through a gate, and removing the molding frame after the resin is cooled (step S3). It is desirable to arrange the thickness h1 (see FIG. 5) of the cable fixing part 60 so that the outer insulative members 54 of the coaxial cables 50 are exposed from the top face f4, from a viewpoint of keeping the diameter of the imaging device 100 small. Similarly, as for the width h2 (see FIG. 4) of the cable fixing part 60, although it is acceptable even when the outer insulative members 54 of the coaxial cables 50 positioned on the outside are exposed as long as it is possible to fix the simple cable 55 and the coaxial cables 50, it is preferable to form lateral faces f5 and f6 each having a flat surface so that the outer insulative members 54 are covered by the cable fixing part 60, from a viewpoint of easiness for holding the cable structure 40.

The first openings 64 and the second openings 65 are formed from the top face f4 side and the bottom face f3 side of the cable fixing part 60, by performing laser processing while applying a mask (step S4). The step part 63 may be shaped by using a molding frame or may be formed at the time of forming the openings.

To connect the cable structure 40 to the second circuit board 30, while the first openings 64 and the second openings 65 of the cable fixing part 60 are arranged to be positioned over the core wire connection electrode 32 and the shield wire connection electrode 33 of the second circuit board 30, the core wires 56 and 51 and the shield wires 53 are connected to the core wire connection electrode 32 and to the shield wire connection electrode 33, respectively, by using solder 34. In the first embodiment, when making the connection, the solder 34 is melted by applying heat with a heating tool from above the cable fixing part 60. However, because it is possible to apply the heat while keeping the heating tool in direct contact with the core wires 56 and 51 and the shield wires 53, there is no need to apply the heat for a long period of time. It is therefore possible to reduce the thermal damage that may be caused to the imaging element 10, electronic component parts, and the like.

Further, because the simple cable 55 and the coaxial cables 50 to be connected are fixed while the positions thereof are aligned by the cable fixing part 60, it is possible to perform the connecting work more easily than individually connecting the simple cable 55 and the coaxial cables 50. Further, in the first embodiment, by arranging the step part 63 of the cable structure 40 to abut against the board step part 31 of the second circuit board 30, it is possible to easily align positions in the optical axis direction. In addition, because it is possible to establish the connection to the core wire connection electrode 32 and to the shield wire connection electrode 33 without bending the core wires 56 and 51, it is possible to reduce the possibility of having contact failures.

In the first embodiment described above, the simple cable 55 is arranged between the coaxial cables 50 in the cable structure 40. However, possible embodiments are not limited to this example. The coaxial cables 50 may be arranged next to each other. When the coaxial cables 50 are arranged next to each other, there is no need to provide one second opening 65 for each of the coaxial cables 50, and it is therefore acceptable to provide a single opening.

Figure 9:
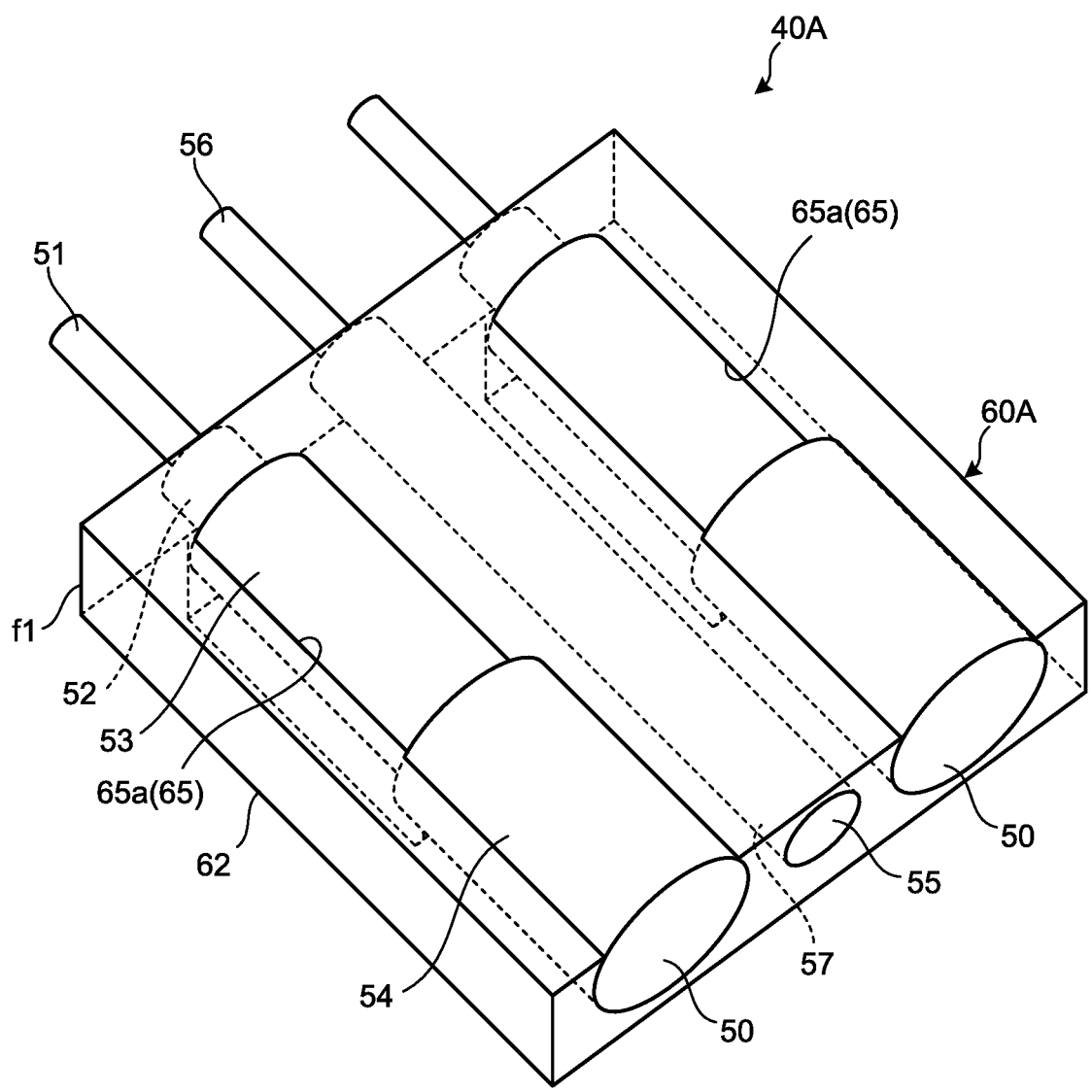
FIG. 9 is a perspective view of a cable structure according to a modification example of the first embodiment.
Figure 10:
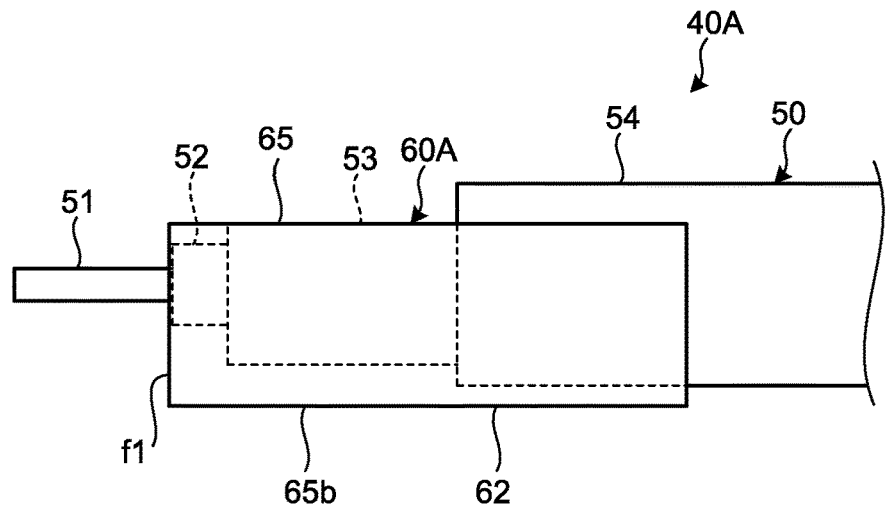
FIG. 10 is a side view of the cable structure illustrated in FIG. 9.

Further, in the first embodiment above, the core wires 56 and 51 are fixed and protected by the first fixing part 61; however, it is also acceptable to expose the entirety of the core wires 56 and 51 without providing the first fixing part 61. FIG. 9 is a perspective view of a cable structure 40A according to a modification example of the first embodiment. FIG. 10 is a side view of the cable structure 40A illustrated in FIG. 9.

A cable fixing part 60A includes only the second fixing part 62 that fixes the outer covering 57 positioned on the proximal end side relative to the exposed core wire 56 of the simple cable 55, as well as the inner insulative members 52, the shield wires 53, and the outer insulative members 54 of the coaxial cables 50. The entirety of parts of the core wire 56 of the simple cable 55 and the core wires 51 of the coaxial cables 50 where the covering parts are removed is exposed.

In the modification example of the first embodiment, because it is possible to apply heat while keeping the heating tool in direct contact with the core wires 56 and 51, it is possible to further shorten the heating time. Further, by arranging the front face f1 side of the second fixing part 62 to abut against the board step part 31 of the second circuit board 30, it is possible to easily align positions in the optical axis direction. In addition, because it is possible to establish the connection to the core wire connection electrode 32 without bending the core wires 56 and 51, it is possible to reduce the possibility of having contact failures.

Figure 11:
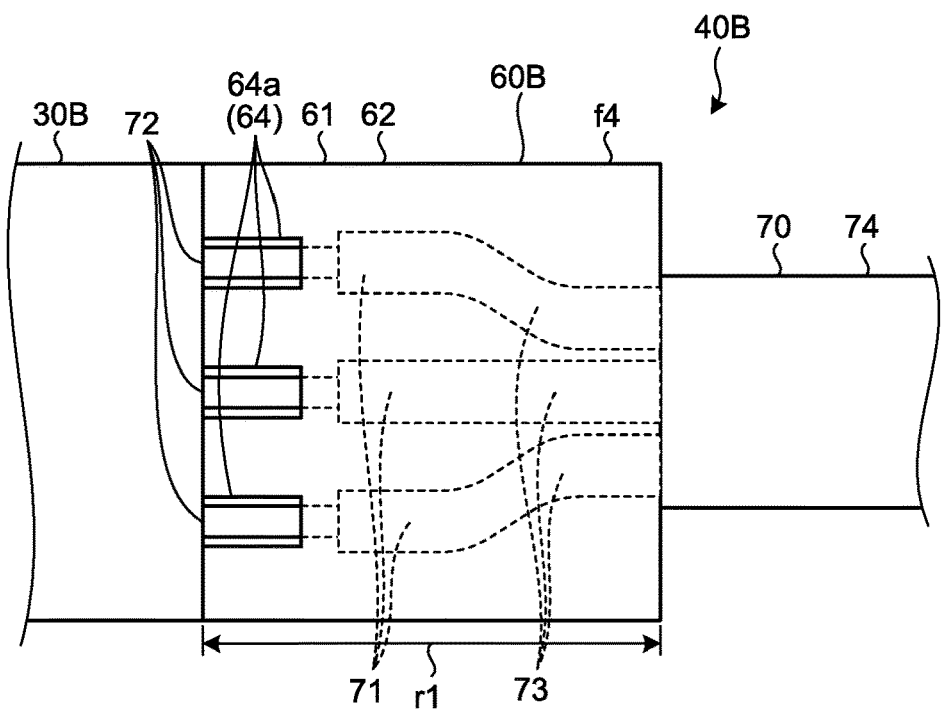
FIG. 11 is a partial top view of an imaging device according to a second embodiment.
Figure 12:
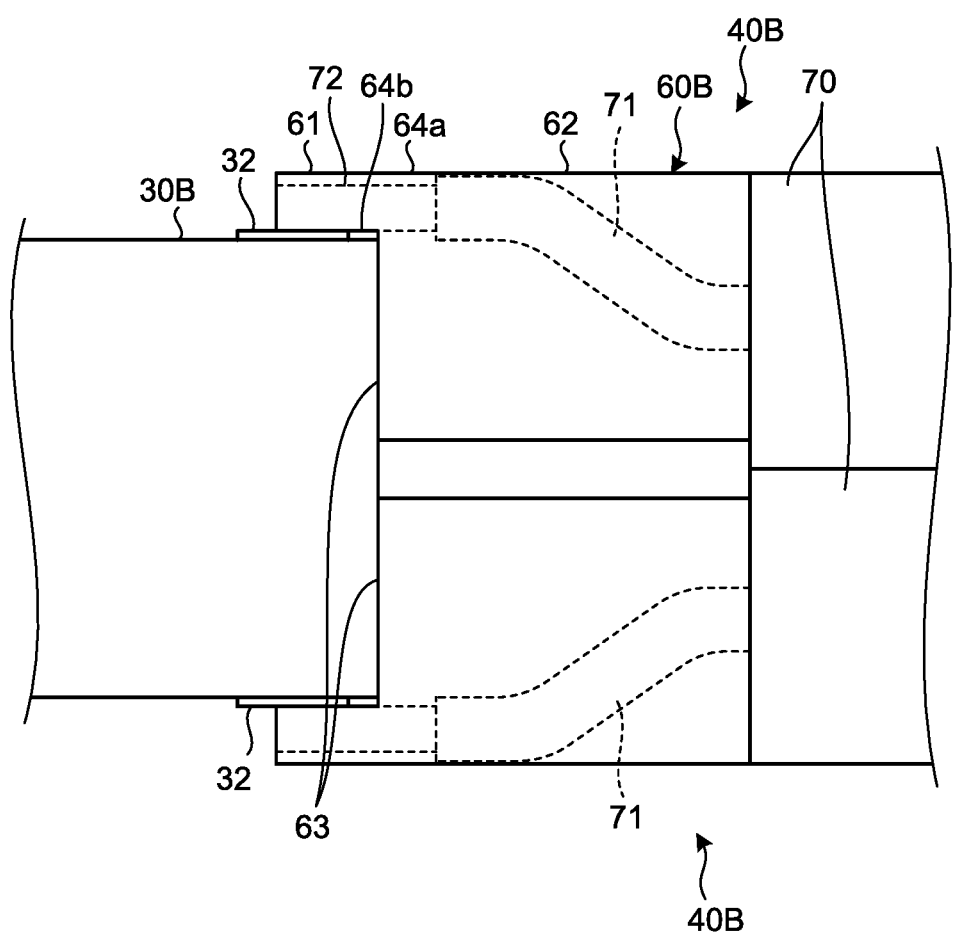
FIG. 12 is a partial side view of the imaging device illustrated in FIG. 11.

In a second embodiment, cable structures are connected to the top face side and to the bottom face side of the second circuit board. FIG. 11 is a partial top view of an imaging device according to the second embodiment. FIG. 12 is a partial side view of the imaging device illustrated in FIG. 11.

A cable structure 40B includes: a cable assembly 70 keeping three simple cables 71 together; and a cable fixing part 60B. The cable fixing part 60B fixes the simple cables 71 having core wires 72 and outer coverings 73 exposed as a result of removing an overall jacket 74 of the cable assembly 70 and the outer coverings 73 of the simple cables 71.

The cable fixing part 60B includes the first fixing part 61 that fixes the core wires 72 of the simple cables 71; and the second fixing part 62 that fixes the outer coverings 73 of the simple cables 71. The second fixing part 62 fixes the simple cables 71 by performing a forming process (a bending and aligning process) thereon so that the simple cables 71 transition from a positional arrangement of being fixed in the cable assembly 70 into another positional arrangement of being positioned with the core wire connection electrode 32.

The first fixing part 61 has the first openings 64 formed therein. The core wires 72 are exposed from the inside of the first openings 64. The core wires 72 are exposed from the top face f4 side (the first top face openings 64*a*) and from the bottom face f3 side (the first bottom face opening 64*b*) of the first openings 64.

The step part 63 is formed on the bottom face f3 side of the cable fixing part 60B, between the first fixing part 61 and the second fixing part 62.

Core wire connection electrodes 32 are formed on the top face side and on the bottom face side of a second circuit board 30B. The cable fixing part 60B is connected to each of the core wire connection electrodes 32 provided on the top face side and on the bottom face side.

According to the second embodiment, the simple cables 71 are fixed by the cable fixing part 60B, while the simple cables 71 from the cable assembly 70 are routed around so as to be formed into the prescribed shape. Because the simple cables 71 are formed and fixed by the cable fixing part 60B, it is easy to establish the connection. In addition, because it is possible to keep short the length r1 (see FIG. 11) of the path used for routing the simple cables 71 around, it is possible to miniaturize the imaging device.

Further, similarly to the first embodiment, because it is possible to apply the heat while keeping the heating tool in direct contact with the core wires 72, it is possible to shorten the heating time. Further, by arranging the step part 63 to abut against the board step part 31 of the second circuit board 30B, it is possible to easily align positions in the optical axis direction. In addition, because it is possible to establish the connection to the core wire connection electrodes 32 without bending the core wires 72, it is possible to reduce the possibility of having contact failures.

In the second embodiment, the simple cables 71 from the cable assembly 70 are routed around and formed by the cable fixing part 60B; however, possible embodiments are not limited to this example. It is also acceptable to arrange cables from a composite cable including a simple cable and a coaxial cable to be routed around and be fixed by the cable fixing part. Further, it is also acceptable to connect cable structures having mutually different cables to the top face side and to the bottom face side of the second circuit board 30B.

Figure 13A:
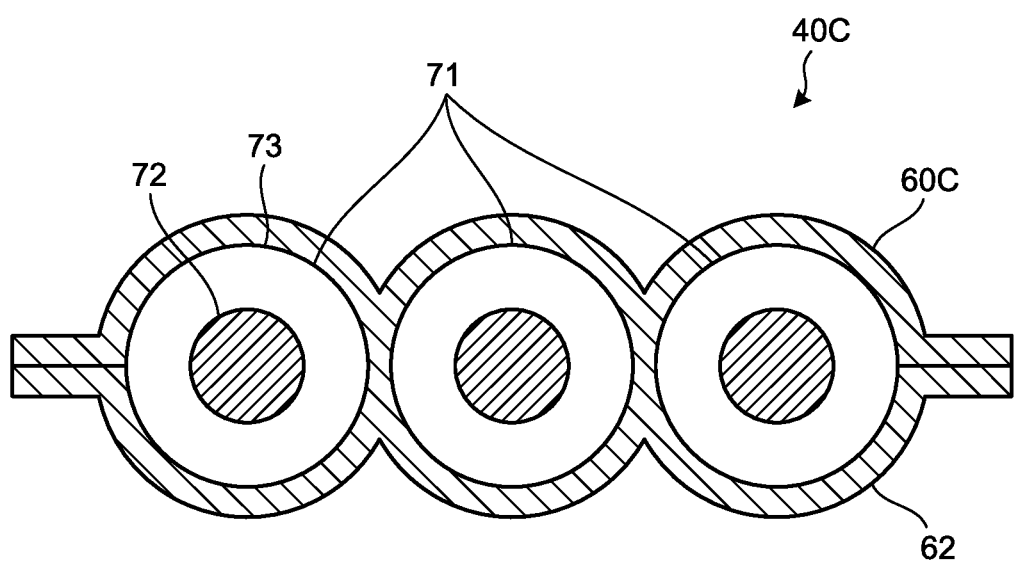
FIG. 13A and FIG. 13B are cross-sectional views of a cable structure according to a third embodiment.
Figure 13B:
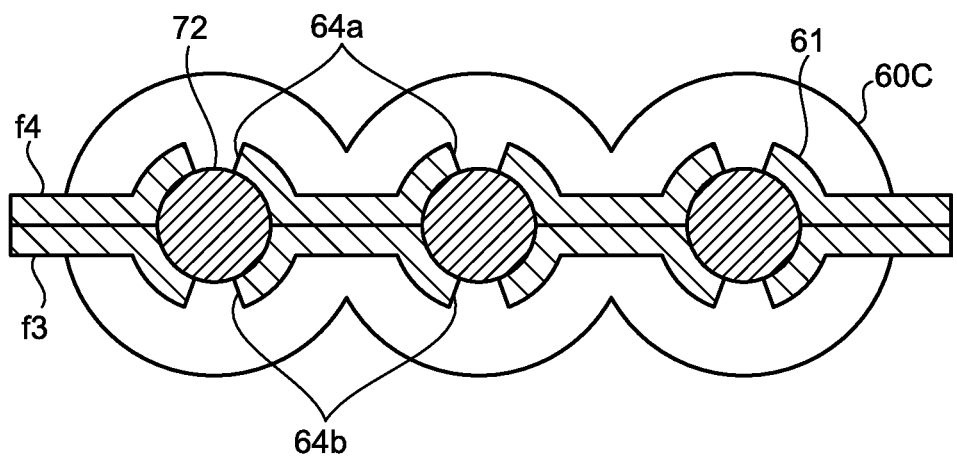

In a third embodiment, a cable fixing part is configured by using a resin film. FIG. 13A and FIG. 13B are cross-sectional views of a cable structure 40C according to the third embodiment. FIG. 13A is a cross-sectional view of the second fixing part 62 in which a cable fixing part 60C fixes the simple cables 71 of which the core wires 72 are covered by the outer coverings 73. FIG. 13B is a cross-sectional view of the first fixing part 61 in which the cable fixing part 60C fixes the core wires 72 from which the outer coverings 73 are removed.

The cable fixing part 60C is formed by covering the simple cables 71 with two sheets of resin film from above and from underneath and performing a lamination forming process.

The first fixing part 61 has the first openings 64 formed therein. The core wires 72 are exposed from the inside of the first openings 64. The core wires 72 are exposed from the top face f4 side and from the bottom face f3 side of the first openings 64.

In the third embodiment, because it is possible to apply heat while keeping the heating tool in direct contact with the core wires 72, it is possible to shorten the heating time.

When the cable structure, the mount module, or the endoscope is used, the conductor parts of the cables are directly heated by a heating tool, while being held by the cable fixing part. Accordingly, it is possible to connect the plurality of cables to the circuit board in an easy and quick manner. Miniaturization is also possible because the length of the path used for routing the cables around is also kept short.

Additional advantages and modifications will readily occur to those skilled in the art. Therefore, the disclosure in its broader aspects is not limited to the specific details and the exemplary embodiments illustrated and described herein. Accordingly, various modifications may be made without departing from the spirit or scope of the general inventive concept as defined by the appended claims and their equivalents.

What is claimed is:

1. A cable structure comprising:
    a plurality of cables each comprising a conductor and an electrically-insulative covering, each conductor being exposed where the covering is removed at one end of each of the plurality of cables; and
    a cable fixing body formed of resin, the cable fixing body being configured to hold the plurality of cables while the conductors of the plurality of cables are aligned, wherein
    the cable fixing body having a fixing part comprising a bottom face opening formed on a bottom face side of the cable fixing body that faces a member to which the cables are connected and a top face opening formed on a top face side of the cable fixing body that opposes the bottom face side, and
    the bottom face opening and the top face opening expose a bottom face side and a top face side of the conductor, respectively, of each of the plurality of cables.

2. The cable structure according to claim 1, wherein each of the plurality of cables is a simple cable, wherein the conductor is a core wire and the covering is an outer covering configured to cover the core wire.

3. The cable structure according to claim 1, wherein
    each of the plurality of cables is a coaxial cable wherein the conductor is a core wire and the covering is an inner insulative member configured to cover the core wire, each of the plurality of cables further comprising a shield wire formed around the inner insulative member, and an outer insulative member configured to cover the shield wire,
    the fixing part comprises a first fixing part configured to fix the core wires;
    the cable fixing body further comprising a second fixing part configured to fix the inner insulative members, the shield wires, and the outer insulative members,
    the second fixing part comprising a second top face opening and a second bottom face opening that expose both of a bottom face side and a top face side, respectively, of the shield wires.

4. The cable structure according to claim 1, wherein the plurality of cables comprise:
    a simple cable, wherein the conductor comprises a core wire and the covering is configured to cover the core wire; and a coaxial cable, wherein the conductor comprises a core wire, the covering comprises an inner insulative member configured to cover the core wire, the coaxial cable further comprising a shield wire formed around the inner insulative member, and an outer insulative member configured to cover the shield wire, the fixing part comprises a first fixing part configured to fix the core wire of the simple cable and core wire of the coaxial cable; and the cable fixing body further comprising a second fixing part configured to fix the covering of the simple cable and to fix the inner insulative member, the shield wire, and the outer insulative member of the coaxial cable, the second fixing part comprises a second top face opening and a second bottom face opening that expose both of a bottom face side and a top face side, respectively, of the shield wire.

5. The cable structure according to claim 4, wherein the core wire of the simple cable and the core wire of the coaxial cable are positioned at an equal distance from the bottom face side of the first fixing part.

6. The cable structure according to claim 2, wherein the cable fixing body comprises a step between a bottom face of the first fixing part and a bottom face of the second fixing part.

7. The cable structure according to claim 3, wherein the cable fixing body comprises a step between a bottom face of the first fixing part and a bottom face of the second fixing part.

8. The cable structure according to claim 4, wherein the cable fixing body comprises a step between a bottom face of the first fixing part and a bottom face of the second fixing part.

9. A cable structure comprising:
a plurality of coaxial cables each comprising a core wire, an inner insulative member configured to cover the core wire, a shield wire formed around the inner insulative member, and an outer insulative member configured to cover the shield wire,
a cable fixing body formed of resin, the cable fixing body being configured to hold the plurality of cables while the conductors of the plurality of cables are aligned, wherein
the cable fixing body is configured to only fix the inner insulative members, the shield wires, and the outer insulative members,
the cable fixing body having a fixing part comprising a bottom face opening formed on a bottom face side of the cable fixing body that faces a member to which the cables are connected and a top face opening formed on a top face side of the cable fixing body that opposes the bottom face side, and
the bottom face opening and the top face opening expose a bottom face side and a top face side of the shield wire, respectively, of each of the plurality of cables.

10. The cable structure according to claim 9, further comprising a simple cable having a core wire and a covering configured to cover the core wire;
wherein the fixing part is also configured to only fix the covering of the simple cable.

11. A mount module comprising:
the cable structure according to claim 1; and
a substrate comprising a plurality of electrodes to which the plurality of cables are to be connected, wherein
the bottom face side of the conductor for each of the plurality of cables is electrically connected to a respective electrode of the plurality of electrodes.

12. An endoscope comprising:
an insertion part comprising an imaging device provided on the substrate at a distal end of the insertion part, the imaging device comprising:
an imaging element configured to receive light and generate an electrical signal by performing a photoelectric conversion; and
the mount module according to claim 11.

13. The mount module according to claim 11, wherein
the plurality of cables comprises at least one coaxial cable, wherein the conductor is a core wire and the covering is an inner insulative member configured to cover the core wire, the at least one coaxial cable further comprising a shield wire formed around the inner insulative member, and an outer insulative member configured to cover the shield wire;
the substrate comprises:
a core wire connection electrode and a shield wire connection electrode to which the core wire and the shield wire of the at least one coaxial cable are to be connected, respectively; and
a substrate step formed between the core wire connection electrode and the shield wire connection electrode,
wherein a step formed in the cable fixing body of the cable structure is arranged to abut against the substrate step.

14. The mount module according to claim 11, wherein
the plurality of electrodes are formed on a top face and on a bottom face of the substrate, and
the cable structure is connected to the top face and to the bottom face of the substrate via the plurality of electrodes.

* * * * *